United States Patent
Burkinshaw et al.

[11] Patent Number: 6,159,216
[45] Date of Patent: Dec. 12, 2000

[54] COMBINATION TIBIAL PREPARATION INSTRUMENTATION

[75] Inventors: Brian D. Burkinshaw, Pflugerville; Richard J. Kana, Lexington, both of Tex.

[73] Assignee: Sulzer Orthopedics Inc., Austin, Tex.

[21] Appl. No.: 09/150,304

[22] Filed: Sep. 9, 1998

[51] Int. Cl.[7] .................................................. A61B 17/58
[52] U.S. Cl. ............................................................ 606/88
[58] Field of Search ................................ 606/84, 88, 80, 606/102, 87, 96, 90

[56] References Cited

U.S. PATENT DOCUMENTS

| | | | |
|---|---|---|---|
| 5,282,866 | 2/1994 | Cohen et al. | 623/20 |
| 5,342,367 | 8/1994 | Ferrante et al. | 606/86 |
| 5,356,414 | 10/1994 | Cohen et al. | 606/88 |
| 5,454,816 | 10/1995 | Ashly | 606/88 |
| 5,609,642 | 3/1997 | Johnson et al. | 623/20 |
| 5,613,970 | 3/1997 | Houston et al. | 606/88 |
| 5,634,927 | 6/1997 | Houston et al. | 606/96 |
| 5,688,281 | 11/1997 | Cripe et al. | 606/88 |
| 5,690,636 | 11/1997 | Wildgoose et al. | 606/88 |
| 5,733,290 | 3/1998 | McCue et al. | 606/85 |
| 5,769,854 | 6/1998 | Bastian et al. | 606/88 |

FOREIGN PATENT DOCUMENTS 0 474 320 A1  11/1992  European Pat. Off. .

OTHER PUBLICATIONS

Protek, Surgical Technique for Wallaby Total Knee Prosthesis, Edition Jan. 1994, pp. 14–17.
Osteonics, Palm Beach Instruments—Surgical Procedures, pp. 24–31.
Johnson & Johnson Orthopaedics, Primary Cruciate–Retaining & Cruciate–Substituting Procedures, 25–36.
U.S. Medica Products, Inc., Consensus Knee System—Surgical Protocol, p. 7–10.

*Primary Examiner*—Michael Buiz
*Assistant Examiner*—(Jackie) Tan-Uyen T. Ho
*Attorney, Agent, or Firm*—Philip S. Lyren; Kenneth S. Barrow

[57] ABSTRACT

A tibial preparation instrument including a baseplate trial having an opening formed therein. A removable handle is attached to the baseplate trial. A keel broach trial is shaped for insertion into the opening. A broach guide is provided for mounting on the baseplate trial. The broach guide includes an attachment member for attachment to the keel broach trial for angularly guiding the keel broach trial through the opening to a seated position on the baseplate trial, whereby the keel broach trial secures the baseplate trial on a tibial plateau.

20 Claims, 5 Drawing Sheets

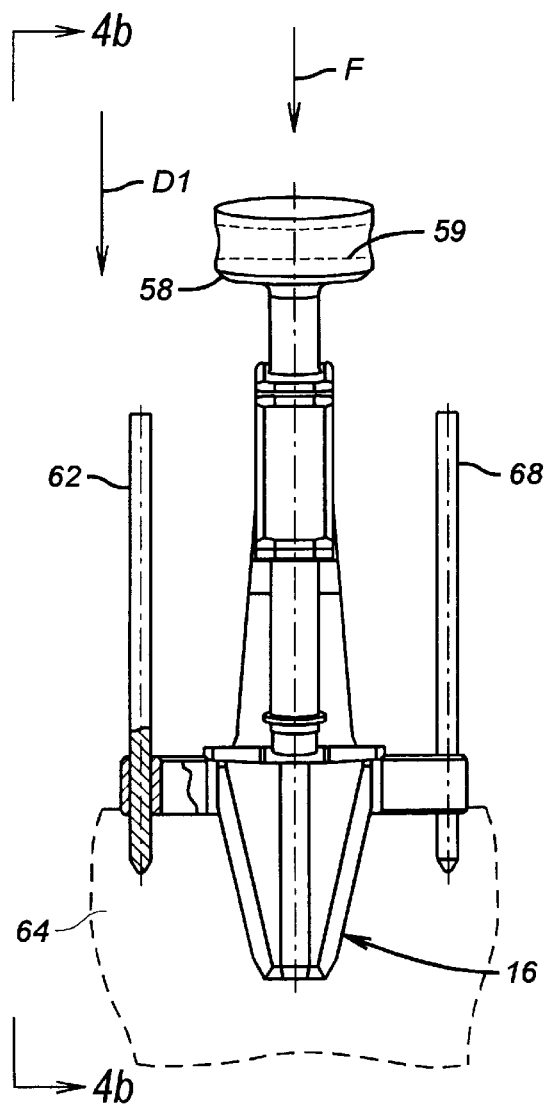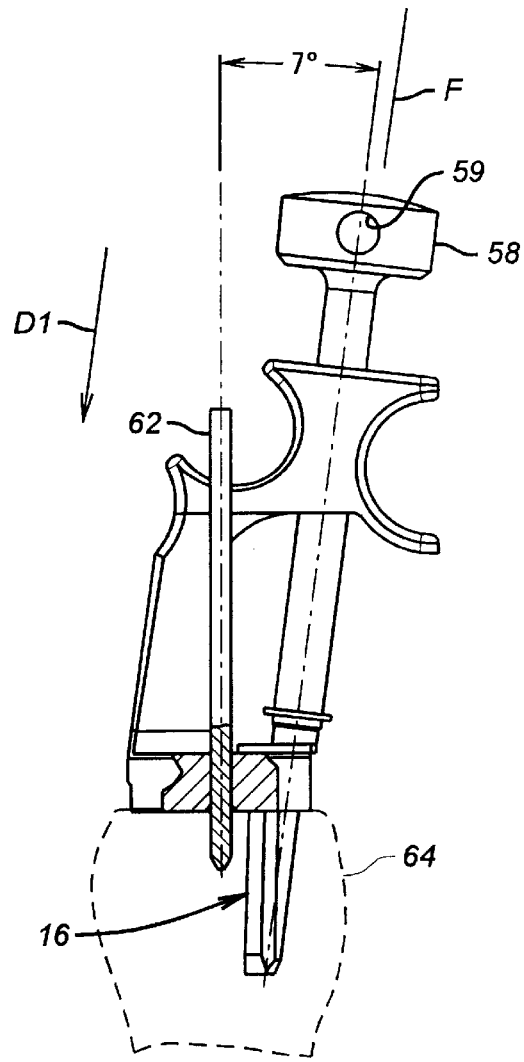
FIG. 4a   FIG. 4b

COMBINATION TIBIAL PREPARATION INSTRUMENTATION

BACKGROUND

The disclosures herein relate generally to orthopedic surgical instruments and more particularly to a method and apparatus for preparing a tibial bone for implantation of a tibial prosthesis.

In operating rooms, space is a valuable asset, and in most operating rooms, space is very limited. The more surgical instruments required for a procedure, the more space required to lay them out with their cases. Costs associated with the time spent in the operating room are very high. Any means, whether by instrumentation and/or technique to help eliminate operating room time would be desirable. There are numerous instrumentation systems from numerous orthopedic suppliers available for tibia preparation dependent on the style of implant. Other systems offer similar looking devices that are used individually for tibia preparation.

For example, U.S. Pat. No. 5,609,642 discloses a method of implanting a femoral and tibial knee prosthesis and instruments for surgically implanting the femoral and tibial prosthesis component. The method includes the formation of a plurality of surgical cuts on the patient's distal femur. A trial femoral prosthesis is then fitted to the surgically prepared distal femur. The trial prosthesis has a femoral articulating surface and a non-articulating surface that fits the patient's distal femur at the surgical cuts. A surgeon then forms a transverse cut on the patient's proximal tibia. The surgeon places a tibial trial prosthesis on the patient's proximal tibia, the trial prosthesis includes a tibial trial stem that fits the patient's intramedullary canal, a tibial trial metallic tray or plate, and a plastic trial insert that fits the tibial tray or plate. The plastic insert includes a tibial articulating surface that can articulate with the femoral articulating surface. The respective articulating surfaces are placed in contact and the surgeon then moves the patient's knee through a full range of motion. During this movement of patient's knee through a full range of motion, the surgeon uses a lever that is attached to the trial tibial prosthesis to rotate the trial tibial prosthesis about its stem. The surgeon can try different rotational positions of the tibial trial prosthesis each time moving the knee through a full range of motion to ensure proper orientation and an accurate fit.

In U.S. Pat. No. 5,690,636, a punch system is provided for preparing a keel cavity in a tibial bone for implantation of a prosthesis. The system provides a modular punch system providing a logical step-by-step approach to cutting, punching, and/or forming the tibial bone. The system includes a quick release punch guide for attaching to a tibial tray trial component of a surgical instrument system for implanting artificial knees, and a universal quick release handle for attaching or detaching a punch from a handle or slap hammer.

In a typical procedure, once the tibia plateau has been cut, a sizing template is used to determine the correct implant size and positioning. Pin holes may be drilled and filled with pins to hold the template in position. The sizing template may then be used as a base for a reamer/broach guide to prepare the canal for the implant stem. Additional pin holes may be drilled for use with the reamer/broach guide. Typical systems also require an individual reamer/broach guide for each size template, stem or baseplate implant used. Depending on the number of sizes offered, this usually amounts to a comparable number of individual instruments. Typically, the template is then removed and a trial tibia baseplate is then placed onto the prepared bone. There are usually individual trials for each size implant offered, which adds additional instruments to the system.

Therefore, what is needed is a method and apparatus for preparing a tibial bone for implementation of a tibial prosthesis which reduces the number of tibial preparation instruments required, and also reduces the overall time for the procedure thereby resulting in reduced operating room time.

SUMMARY

One embodiment, accordingly, provides an apparatus and a method for preparing a tibia for a tibial implant by reducing the number of parts needed for accomplishing the task and by substantially reducing the number of steps typically required in such a procedure. To this end, a tibial preparation apparatus includes a baseplate trial including an opening formed therein. A keel broach trial is shaped for insertion into the opening. A broach guide is provided for supporting and guiding the keel broach trial through the opening.

A principal advantage of this embodiment is that individual instruments are integrated together so that the tibial broach remains in the bone and functions as the keel/stem component of the tibial trial, therefore reducing the total number of instruments and time required for the procedure.

BRIEF DESCRIPTION OF THE DRAWING FIGURES

FIG. 4a is an anterior view illustrating an embodiment of the assembled tibial preparation instrument.

FIG. 4b is a medial/lateral view taken along the line 4b—4b of FIG. 4a.

DETAILED DESCRIPTION

Figure 1:
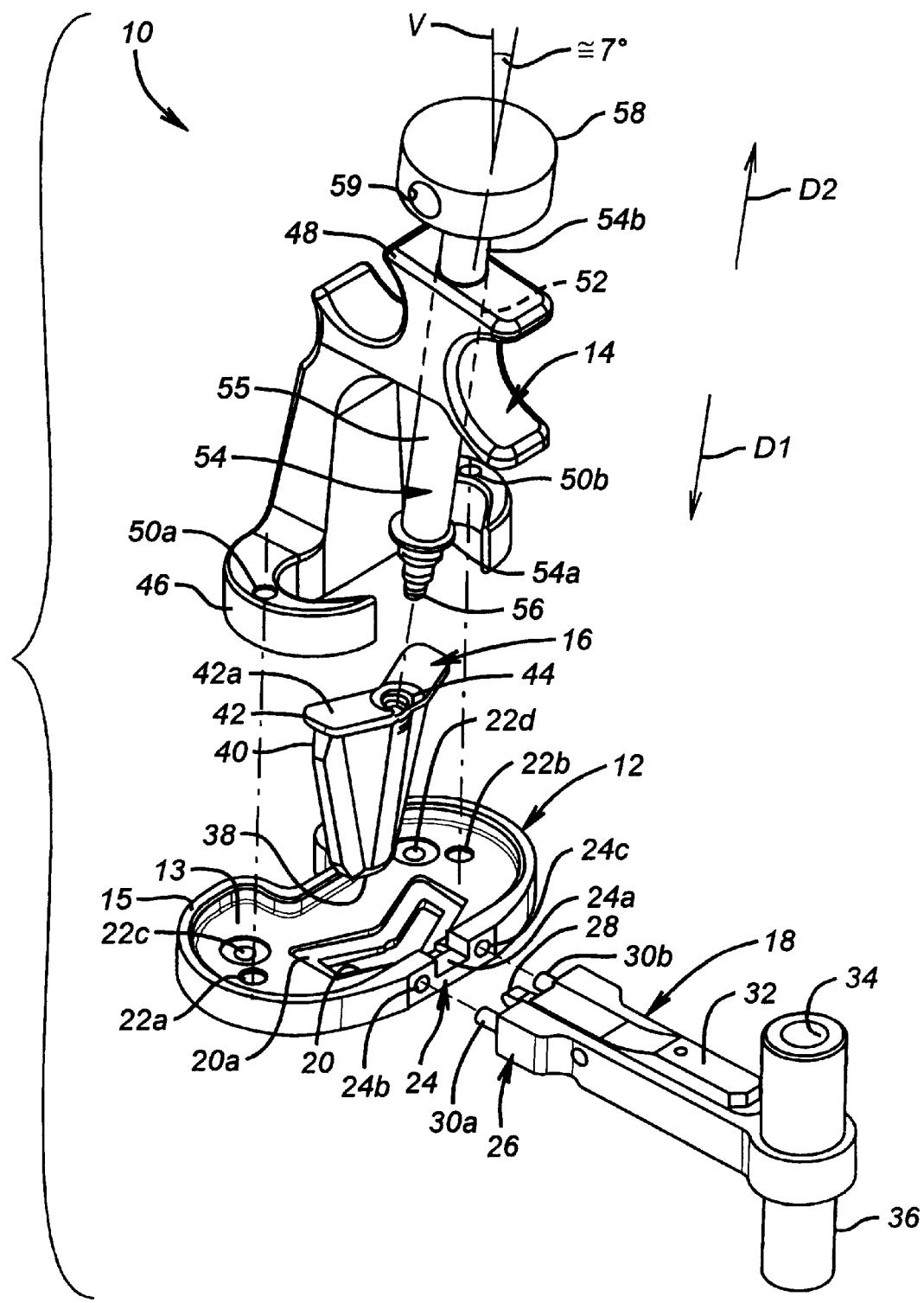
FIG. 1 is an exploded perspective view illustrating an embodiment of a tibial preparation instrument.

An apparatus generally designated 10 in FIG. 1 is provided as an instrument for tibial insert preparation, and includes a baseplate trial member 12, a broach guide member 14, a keel broach trial member 16 and a removable or modular handle 18.

Baseplate trial member 12 includes a planar surface 13 and a raised edge 15. Planar surface 13 includes an opening 20 of a generally chevron shape for receiving the similarly shaped keel broach trial 16. Opening 20 is surrounded by a lip portion 20a recessed in planar surface 13. Also, a plurality of apertures 22a, 22b, 22c and 22d are formed through planar surface 13. A receiver 24 is formed in raised edge 15 and includes a groove 24a extending through a portion of raised edge 15, and a pair of apertures 24b and 24c, extending through edge 15 adjacent opposite sides of groove 24a. Two of the apertures, i.e. apertures 22a and 22b, are provided to receive a drill for forming pin holes for inserting temporary pins in a tibial plateau, not shown in FIG. 1, whereas apertures 22c and 22d are provided for forming a pair of recesses in the tibial plateau for receiving a similarly aligned pair of well-known stabilizing pegs attached to the baseplate of the tibial insert, also not shown.

Handle 18 is known and includes an attachment end 26 including a resiliently biased hook 28 for engagement with groove 24a, and a pair of stabilizing pegs 30a and 30b adjacent opposite sides of hook 28 for engagement with apertures 24b and 24c. An extension 32 is attached to pivot so as to release hook 28 from engagement with groove 24a of edge 15. An alignment rod aperture 34 is provided in an alignment rod support 36 on handle 18, for uses not discussed further in the embodiments herein.

The keel broach trial member 16 is a generally wedge-shaped device having a chevron-like cross-section. A first end 38 of keel broach trial 16 is tapered for insertion into soft bone material in an associated tibia, and a second end 40 includes a flange 42 for seated engagement with the recessed lip portion 20a surrounding opening 20. Flange 42 is of a thickness substantially equal to the depth of recess 20a so that when seated, a surface 42a of flange 42 is flush with planar surface 13 of baseplate trial member 12. A threaded receiver 44 is formed in keel broach trial member 16 for receiving a movable portion of the broach guide member 14, to be discussed below.

Broach guide member 14 includes a base 46 and an angled attachment member guide 48 extending from the base 46. The base 46 includes a pair of pin receiving apertures 50a and 50b formed therethrough, which align with apertures 22a and 22b, respectively, when base 46 is seated on planar surface 13 of baseplate trial member 12. Guide 48 includes a guide sleeve 52 angled at about seven (7) degrees from a vertical axis designated V. An attachment member 54 includes a shaft portion 55 slidably mounted in sleeve 52 for reciprocating movement in directions indicated by a pair of directional arrows designated D1 and D2. A first end 54a of attachment member 54 includes a threaded tip portion 56 for threaded engagement into receiver 44 of keel broach trial member 16. A second end 54b of attachment member 54 includes a grip member 58 having an aperture 59 transversely extending therethrough for receiving a tommy bar or a slap hammer (not shown) used for retracting a tibial trial prior to securing the tibial implant in place.

Figure 2:
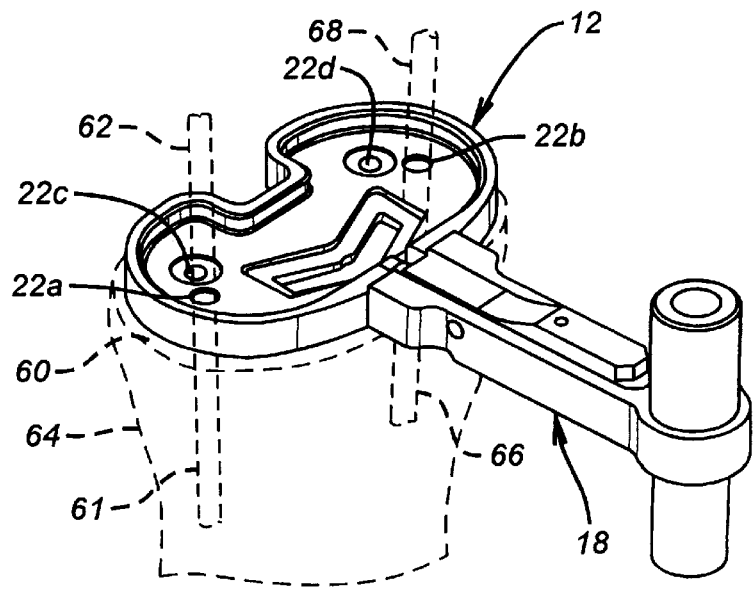
FIG. 2 is a perspective view illustrating an embodiment of a baseplate trial and a modular handle.

The baseplate trial 12, FIG. 2, is attached to the handle 18 and is used as a sizing template by placing the baseplate trial 12 on a tibial plateau 60, previously prepared. If necessary, this procedure is repeated by attaching handle 18 to various sizes of the baseplate trial 12 until an appropriate baseplate size is determined. A first pin hole 61, FIG. 2, is drilled through, for example, aperture 22a, and a pin 62 is inserted through aperture 22a and into an associated tibia 64. If baseplate trial 12 is suitably located, a second pin hole 66 is drilled through, for example, aperture 22b, and a pin 68 is inserted through aperture 22b and into tibia 64. Additional holes may also be drilled in tibia 64 using apertures 22c and 22d as a template. These additional holes may be used to receive the previously mentioned stabilizing pegs extending from the tibial baseplate (not shown). Handle 18 may be removed at this point if desired.

Figure 3:
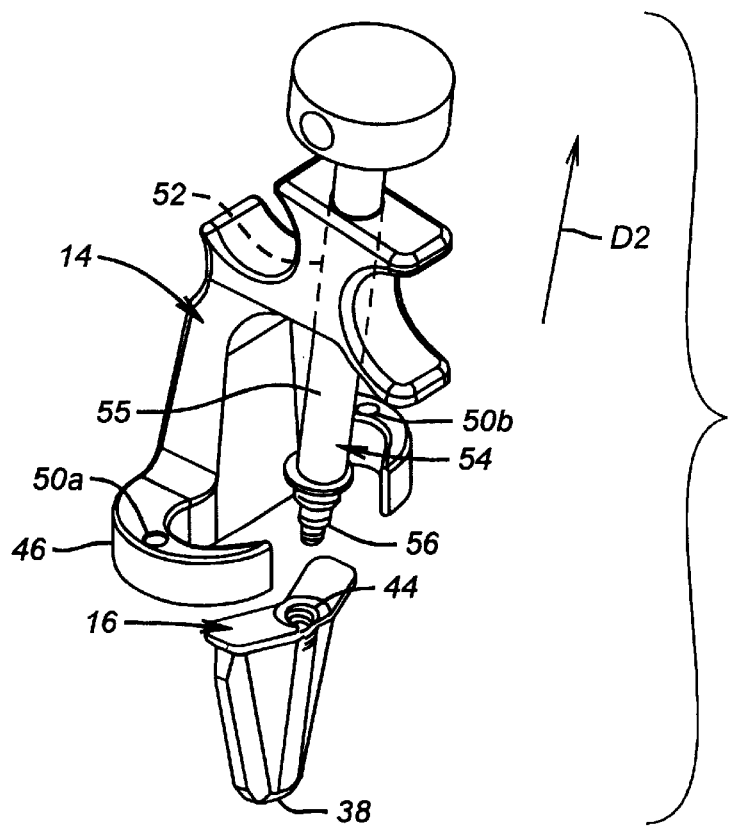
FIG. 3 is an exploded perspective view illustrating an embodiment of a broach guide and a keel broach trial.

An appropriately sized keel broach trial 16, for matching the baseplate trial 12, may be threadably attached to attachment member 54, FIG. 3, by threading tip portion 56 into receiver 44. Attachment member 54 is moved in direction D2 to position first end 38 of keel broach trial 16 adjacent base 46 of broach guide member 14. This is accomplished by sliding shaft 55 within sleeve 52. Pin apertures 50a and 50b of broach guide 14 are slidingly engaged onto pins 62 and 68 until base 46 seats on planar surface 13, see also FIG. 4.

Figure 4:
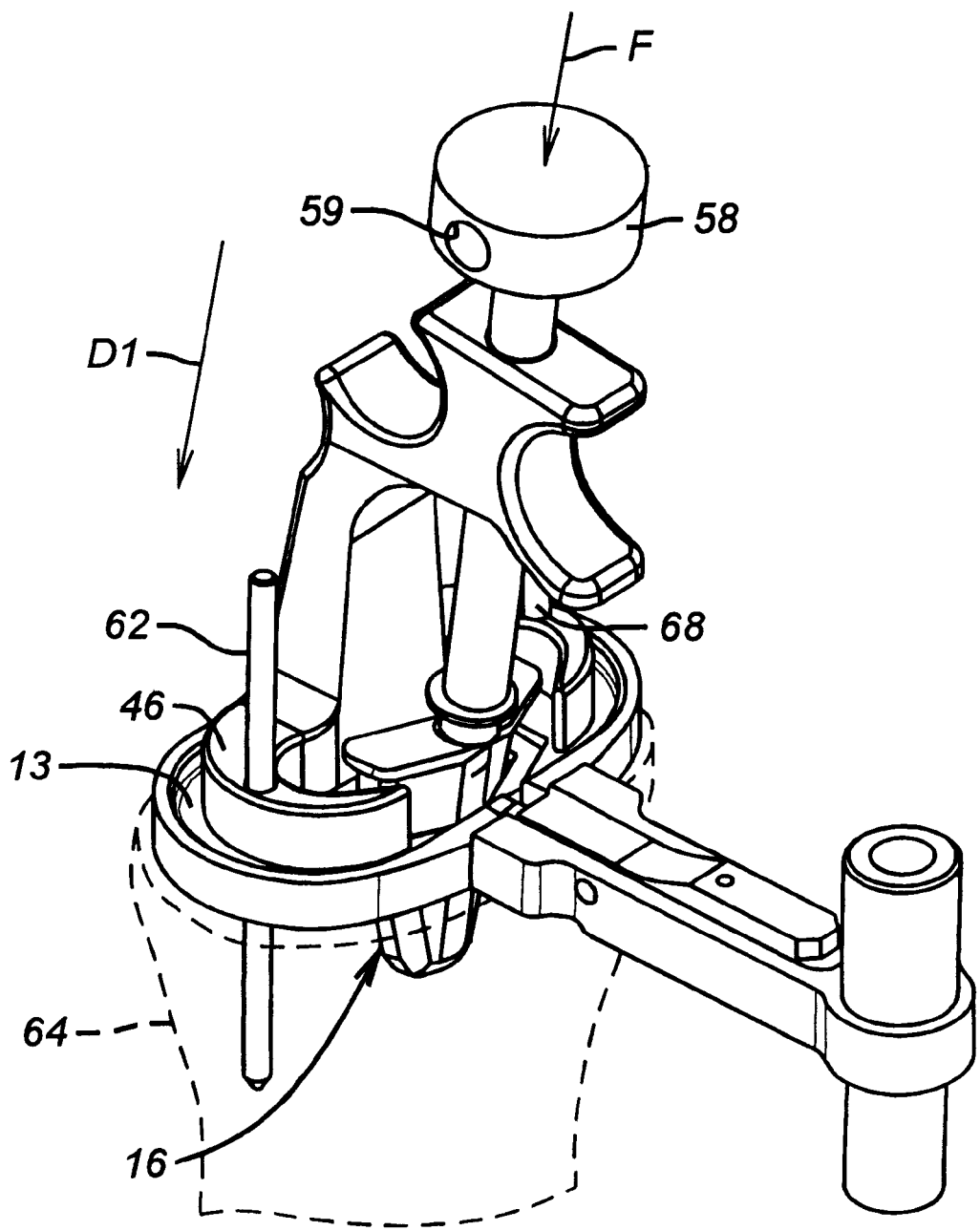
FIG. 4 is a perspective view illustrating an embodiment of the assembled tibial preparation instrument.
Figure 5:
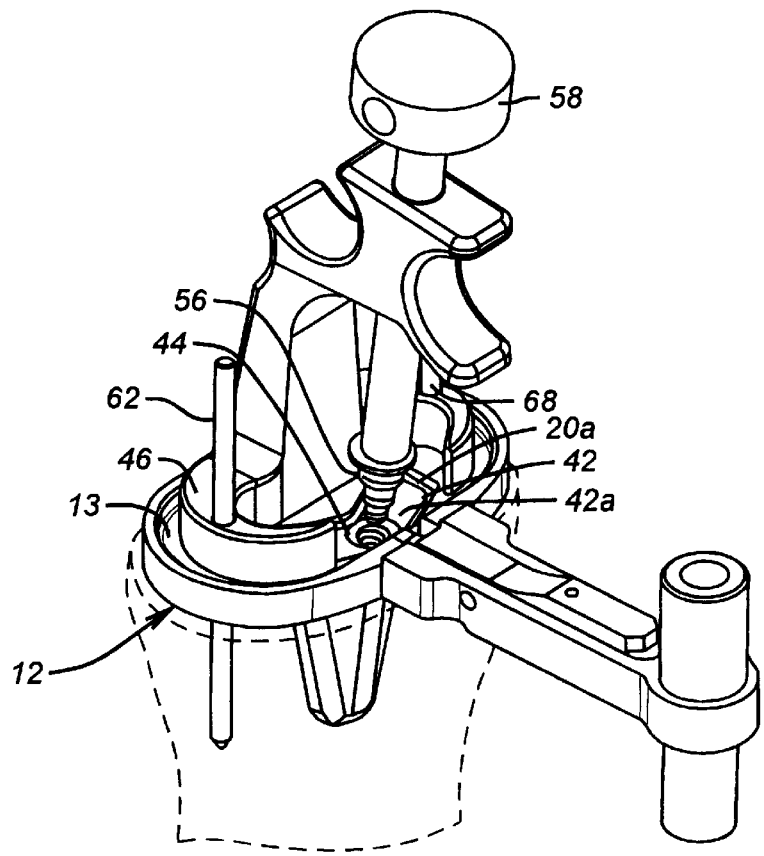
FIG. 5 is another perspective view illustrating an embodiment of the assembled tibial preparation instrument.
Figure 6:
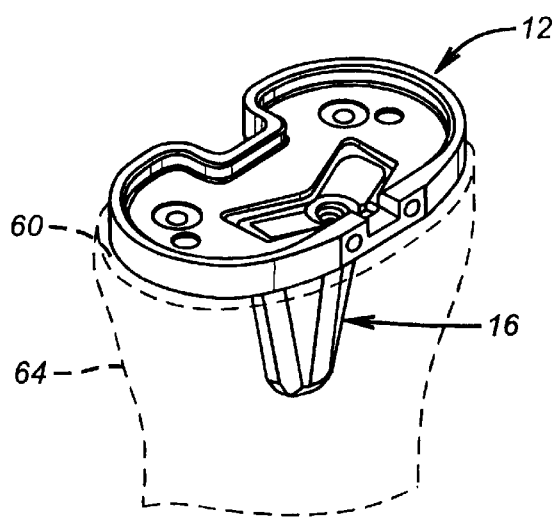
FIG. 6 is a perspective view illustrating an embodiment of the baseplate trial attached to a tibia by the keel broach trial.

A force designated F is then applied to grip member 58, FIG. 4, to urge keel broach trial member 16 in direction D1 into soft bone material within tibia 64, see also FIGS. 4a and 4b. Flange 42, FIG. 5, of keel broach trial member 16 is now seated on lip portion 20a such that surface 42a is substantially flush with planar surface 13. Grip member 58, may then be rotated to detach threaded portion 56 from receiver 44. Base 46 may be removed from baseplate trial 12 by removing pins 62, 68. As a result, baseplate trial 12, FIG. 6, is secured on tibial plateau 60 of tibia 64 by means of keel broach trial 16 being wedged into soft bone material in tibia 64. At this point the surgeon can select the appropriate thickness for a trial insert to be mounted on the baseplate trial in preparation for trial reduction. Removal of baseplate trial 12 and keel broach trial 16 may be accomplished by various known means including threaded re-attachment of broach guide 14 to keel broach trial 16, attaching a slap-hammer or tommy bar to aperture 59 in grip member 58, for urging keel broach trial 16 out of tibia 64.

In operation, the baseplate trial is first used as a sizing template including a drill guide and an alignment guide. As a drill guide, the template aids the surgeon in drilling holes at the proper locations and angle for the corresponding implant. The modular handle accepts an alignment rod to aid in axial alignment. Once the implant size has been determined, the corresponding keel broach/trial size is attached to the broach guide. The broach guide is attached to the template with 2 standard pins. Proper angle and location of the keel broach/trial will be assured using the broach guide. The keel broach/trial is impacted through the template into the bone. A flange on the keel broach/trial fits into a recessed area on the template to determine proper depth. The broach guide and the modular handle are removed, leaving behind the tibia baseplate trial and keel broach/trial. In addition to broaching for the implant, the keel broach/trial functions as an anchor keeping the baseplate trial stable through trial reductions.

As a result, one embodiment provides a tibial preparation apparatus including a baseplate trial having an opening formed therein. A keel broach trial is shaped for insertion into the opening. A broach guide is provided for supporting and guiding the keel broach trial through the opening.

Another embodiment provides a tibial implant preparation apparatus including a baseplate trial including an opening formed therein. A broach guide is mounted on the baseplate trial and includes an attachment member. A keel broach trial is attached to the attachment member and is angularly aligned with the opening. The attachment member is movable for advancing the keel broach trial through the opening in the baseplate trial.

Another embodiment provides a preparation instrument for a tibial insert including a baseplate trial including an opening formed therein. A removable handle is attached to the baseplate trial. A keel broach trial is shaped for insertion into the opening. A broach guide is mounted on the baseplate trial and is attached to the keel broach trial for angularly guiding the keel broach trial through the opening to a seated position on the baseplate trial.

A further embodiment provides a method of preparing a tibia for an implant including locating a baseplate trial on a tibial plateau, the trial including an opening formed therein. The baseplate trial is positioned on the tibial plateau with a plurality of pins. A keel broach trial is attached to a broach guide. The broach guide is engaged with the pins for mounting the broach guide on the baseplate trial. The broach guide is then used for advancing the keel broach trial through the opening to a seated position on the baseplate trial.

As it can be seen, the principal advantage of these embodiments are that the sizing template and broach remain on and in the bone. The modular handle is removed from the template, the broach guide is disconnected from the keel/broach and the guide is lifted off the template. The keel/broach has been driven into the tibia canal and serves as an additional means of stabilizing the baseplate trial. The tibia template now replicates the implant and is used for the baseplate trial. The template need not be removed from the bone and replaced with an individual trial. Tibia trial reduction may be performed in the usual manner.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A tibial preparation apparatus comprising:
    a baseplate trial including an opening formed therein and a lip formed as a recess adjacent the opening;
    a keel broach trial shaped for insertion into the opening and having a flange for engaging the lips; and
    a broach guide being removably attachable to the keel broach trial for supporting and guiding the keel broach trial through the opening.

2. The apparatus as defined in claim 1 wherein the baseplate trial includes a plurality of pin apertures formed therethrough.

3. The apparatus as defined in claim 1 wherein the baseplate trial includes a receiver for engaging and supporting attachment of a removable handle.

4. The apparatus as defined in claim 1 wherein the keel broach trial includes a receiver for engaging a movable portion of the broach guide.

5. The apparatus as defined in claim 1 wherein the broach guide includes a base and a movable attachment member.

6. The apparatus as defined in claim 5 wherein the base includes a plurality of pin apertures.

7. The apparatus as defined in claim 6 wherein the broach guide includes an angled attachment member guide.

8. The apparatus as defined in claim 7 wherein the movable attachment member is mounted in the angled attachment member guide and includes an engagement end for engaging the keel broach trial.

9. A tibial implant preparation apparatus comprising:
    a baseplate trial including an opening formed therein and a recess adjacent the opening;
    a broach guide mounted on the baseplate trial and including an attachment member; and
    a keel broach trial having a receiver at one end for removably attaching to the attachment member and angularly aligned with the opening, the attachment member being movable for advancing the keel broach trial through the opening in the baseplate trial, and the one end having a flange with a diameter larger than the opening in the baseplate, the flange abutting against the baseplate to prevent the keel broach trial from passing completely through the opening.

10. The apparatus as defined in claim 9 wherein the baseplate trial includes a plurality of pin apertures formed therethrough.

11. The apparatus as defined in claim 9 wherein the baseplate trial includes a lip portion surrounding the opening.

12. The apparatus as defined in claim 9 wherein the baseplate trial includes a receiver for engaging and supporting attachment of a removable handle.

13. The apparatus as defined in claim 11 wherein the keel broach trial includes a flange for engagement with the lip portion of the baseplate trial.

14. The apparatus as defined in claim 9 wherein the keel broach trial includes a receiver for engaging the attachment member.

15. The apparatus as defined in claim 9 wherein the broach guide includes a base and an angled attachment guide.

16. The apparatus as defined in claim 15 wherein the attachment member is movably mounted in the angled attachment guide.

17. The apparatus as defined in claim 16 wherein the attachment member includes an engagement end for engaging the keel broach trial.

18. The apparatus as defined in claim 15 wherein the base includes a plurality of pin apertures formed therethrough.

19. A preparation instrument for a tibial implant comprising:
    a baseplate trial including an opening formed therein and a recess adjacent the opening;
    a removable handle attached to the baseplate trial;
    a keel broach trial shaped for insertion into the opening and having a flange at one end for abutting against a portion of the baseplate trial to prevent the keel broach trial from passing completely through the opening; and
    a broach guide mounted on the base plate trial and attached to the keel broach trial for angularly guiding the keel broach trial through the opening to a seated position on the baseplate trial.

20. A method of preparing a tibia for an implant comprising the steps of:
    locating a baseplate trial on a tibial plateau, the trial including an opening formed therein and a recess adjacent the opening;
    positioning the baseplate trial on the tibial plateau with a plurality of pins;
    attaching a keel broach trial to a broach guide, the keel broach trial including a flange at one end;
    engaging the broach guide with the pins for mounting the broach guide on the baseplate trial; and
    utilizing the broach guide for advancing the keel broach trial through the opening until the flange abuts the baseplate trial to a seated position.

* * * * *